(12) United States Patent
Dahl et al.

(10) Patent No.: US 7,985,761 B2
(45) Date of Patent: Jul. 26, 2011

(54) DIPHENYLUREA DERIVATIVES AND THEIR USE AS CHLORIDE CHANNEL BLOCKERS OR $BK_{Ca}$ CHANNEL MODULATORS

(75) Inventors: Bjarne H. Dahl, Lynge (DK); Palle Christophersen, Ballerup (DK); Lars Siim Madsen, Sorø (DK)

(73) Assignee: Neurosearch A/S, Ballerup (DK)

( * ) Notice: Subject to any disclaimer, the term of this patent is extended or adjusted under 35 U.S.C. 154(b) by 377 days.

(21) Appl. No.: 12/280,490

(22) PCT Filed: Mar. 9, 2007

(86) PCT No.: PCT/EP2007/052243
§ 371 (c)(1),
(2), (4) Date: Aug. 22, 2008

(87) PCT Pub. No.: WO2007/104719
PCT Pub. Date: Sep. 20, 2007

(65) Prior Publication Data
US 2009/0018172 A1    Jan. 15, 2009

(30) Foreign Application Priority Data

Mar. 14, 2006   (DK) ................................ 2006 00360

(51) Int. Cl.
*A61K 31/4245*   (2006.01)
*C07D 271/07*   (2006.01)
(52) U.S. Cl. ........................................ 514/364; 548/132
(58) Field of Classification Search ........................ None
See application file for complete search history.

(56) References Cited

FOREIGN PATENT DOCUMENTS

| WO | WO-00/24707 A1 | 5/2000 |
|---|---|---|
| WO | WO-2004/046090 A2 | 6/2004 |
| WO | WO-2004/111017 A1 | 12/2004 |
| WO | WO-2005/023237 A1 | 3/2005 |
| WO | WO-2005/023238 A1 | 3/2005 |

*Primary Examiner* — Kamal Saeed
(74) *Attorney, Agent, or Firm* — Birch, Stewart, Kolasch & Birch, LLP

(57) ABSTRACT

The present invention relates to novel diphenylurea derivatives useful as chloride channel blockers or $BK_{Ca}$ channel modulators.

In other aspects the invention relates to the use of these compounds in a method for therapy, and to pharmaceutical compositions comprising the compounds of the invention.

10 Claims, No Drawings

DIPHENYLUREA DERIVATIVES AND THEIR USE AS CHLORIDE CHANNEL BLOCKERS OR BK$_{Ca}$ CHANNEL MODULATORS

TECHNICAL FIELD

The present invention relates to novel diphenylurea derivatives useful as chloride channel blockers or BK$_{Ca}$ channel modulators.

In other aspects the invention relates to the use of these compounds in a method for therapy, and to pharmaceutical compositions comprising the compounds of the invention.

BACKGROUND ART

Chloride channels serve a wide variety of specific cellular functions and contribute to the normal function of i.a. skeletal and smooth muscle cells. Chloride channels are probably found in every cell, from bacteria to mammals. Their physiological tasks range from cell volume regulation to stabilization of the membrane potential, transepithelial or transcellular transport and acidification of intracellular organelles.

Likewise, The Ca$^{2+}$-activated BK channels are present in many cells including most central and peripheral nerve cells, striated muscle cells, cardiac cells, smooth muscle cells of the airways, the vasculature, the gastrointestinal tract and bladder, in endo- and exocrine glands including pancreatic b-cells and in kidney tubules.

There is a continued strong need to provide compounds active as chloride channel blockers or BK$_{Ca}$ channel modulators and with an optimized pharmacological profile. Furthermore, there is a strong need to find effective compounds without unwanted side effects associated with older compounds.

WO 2005/023237 and WO 2005/023238 (Poseidon Pharmaceuticals A/S) describe the use of ERG channel openers for the treatment of hyperexcitability-related neuronal diseases and cardiac arrhythmias. Among the compounds disclosed is 1-(3-trifluoromethyl-phenyl)-3-[2-(5-oxo-4,5-dihydro-[1,2,4]oxadiazol-3-yl)-4-(4'-N,N-dimethylcarbamoyl)-biphenyl]-urea.

SUMMARY OF THE INVENTION

It is an object of the invention to provide novel compounds which act as chloride channel blockers or BK$_{Ca}$ channel modulators.

A further object of the invention is the provision of compounds with a better selectivity. A still further object is the provision of compounds with a better potency.

A further object of the invention is the provision of compounds that act on cell or tissue specific chloride channels or BK$_{Ca}$ channels. A still further object is the provision of compounds that act on specific groups or subtypes of chloride channels.

A still further object is the provision of compound with more optimal pharmacodynamic properties such as kinetic behaviour, bioavailability, solubility and efficacy.

In its first aspect, the invention provides a compound of the general formula I,

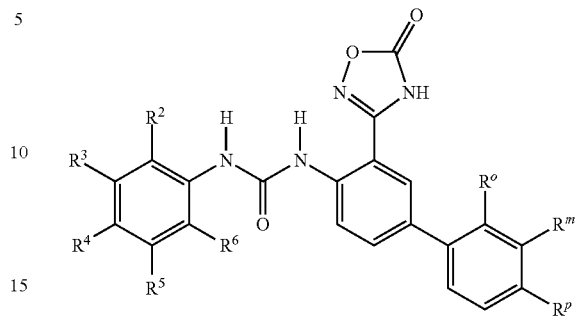

(I)

any of its isomers or any mixture of its isomers, or a pharmaceutically acceptable salt thereof, wherein R$^o$, R$^m$, R$^p$, R$^2$, R$^3$, R$^4$, R$^5$ and R$^6$ are as defined below.

In its second aspect, the invention provides a pharmaceutical composition, comprising a therapeutically effective amount of a compound of the invention, any of its isomers or any mixture of its isomers, or a pharmaceutically acceptable salt thereof, together with at least one pharmaceutically acceptable carrier, excipient or diluent.

In a further aspect, the invention provides the use of a compound of the invention, any of its isomers or any mixture of its isomers, or a pharmaceutically acceptable salt thereof, for the manufacture of a pharmaceutical composition for the treatment, prevention or alleviation of a disease or a disorder or a condition of a mammal, including a human, which disease, disorder or condition is responsive to the blockade of chloride channels or modulation of BK$_{Ca}$ channels—or for the manufacture of a medicament useful for increasing the blood-brain barrier permeability.

In a still further aspect, the invention relates to a method for treatment, prevention or alleviation of a disease or a disorder or a condition of a living animal body, including a human, which disorder, disease or condition is responsive to responsive to blockade of chloride channels or modulation of BK$_{Ca}$ channels, which method comprises the step of administering to such a living animal body in need thereof a therapeutically effective amount of a compound of the invention, any of its isomers or any mixture of its isomers, or a pharmaceutically acceptable salt thereof.

Other objects of the invention will be apparent to the person skilled in the art from the following detailed description and examples.

DETAILED DISCLOSURE OF THE INVENTION

Diphenylurea Derivatives

In its first aspect, the invention provides a chemical compound of formula I,

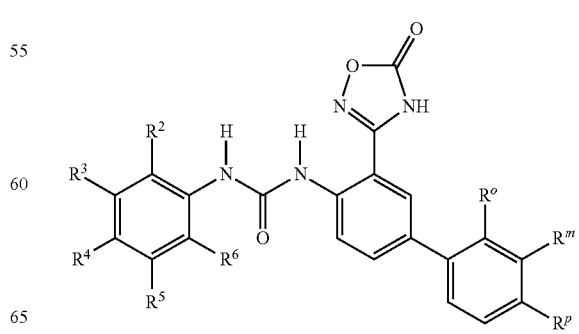

(I)

any of its isomers or any mixture of its isomers, or a pharmaceutically acceptable salt thereof; wherein $R^o$, $R^m$, $R^p$, $R^2$, $R^3$, $R^4$, $R^5$ and $R^6$ independently of each other represent hydrogen, halo, trifluoromethyl, trifluoromethoxy, alkyl or alkoxy.

In one embodiment of the compound of formula I, $R^o$ represents hydrogen; $R^m$ represents hydrogen; and $R^p$ represents halo, trifluoromethyl, trifluoromethoxy, alkyl or alkoxy. In a further embodiment, $R^o$ represents hydrogen; $R^m$ represents hydrogen; and $R^p$ represents halo or trifluoromethyl. In a special embodiment, $R^p$ represents trifluoromethyl.

In a still further embodiment, $R^3$, $R^4$, $R^5$ and $R^6$ represent hydrogen; and $R^2$ represents halo, trifluoromethyl, trifluoromethoxy, alkyl or alkoxy. In a special embodiment, $R^2$ represents halo, such as chloro.

In a further embodiment, $R^2$, $R^4$, $R^5$ and $R^6$ represent hydrogen; and $R^3$ represents halo, trifluoromethyl, trifluoromethoxy, alkyl or alkoxy. In a special embodiment, $R^3$ represents halo, such as bromo.

In a still further embodiment, $R^2$, $R^5$ and $R^6$ represent hydrogen; and $R^3$ and $R^4$ independently of each other represent halo, trifluoromethyl, trifluoromethoxy, alkyl or alkoxy. In a further embodiment, $R^3$ and $R^4$ independently of each other represent halo or trifluoromethyl. In a special embodiment, one of $R^3$ and $R^4$ represents halo, such as chloro, and the other of $R^3$ and $R^4$ represents trifluoromethyl. In a further embodiment, $R^3$ represents trifluoromethyl and $R^4$ represents halo, such as chloro.

In a further embodiment, $R^2$, $R^4$ and $R^6$ represent hydrogen; and $R^3$ and $R^5$ independently of each other represent halo, trifluoromethyl, trifluoromethoxy, alkyl or alkoxy. In a special embodiment, $R^3$ and $R^5$ independently of each other represent halo. In a further embodiment, $R^3$ represents fluoro and $R^5$ represents fluoro.

In a special embodiment the compound of the invention is

N-(3,5-Difluoro-phenyl)-N'-[3-(5-oxo-4,5-dihydro-[1,2,4]oxadiazol-3-yl)-4'-trifluoromethyl-biphenyl-4-yl]urea;

N-(4-Chloro-3-trifluoromethyl-phenyl)-N'-{3-(5-oxo-4,5-dihydro-[1,2,4]-oxadiazol-3-yl)-4'-trifluoromethyl-biphenyl-4-yl}urea;

N-(3-Bromo-phenyl)-N'-{3-(5-oxo-4,5-dihydro-[1,2,4]-oxadiazol-3-yl)-4'-trifluoromethyl-biphen-4-yl}urea;

N-(2-Chloro-phenyl)-N'-{3-(5-oxo-4,5-dihydro-[1,2,4]-oxadiazol-3-yl)-4'-trifluoromethyl-biphenyl-4-yl]urea;

or a pharmaceutically acceptable salt thereof.

Definition of Substituents

In the context of this invention halo represents fluoro, chloro, bromo or iodo.

Alkyl means a straight chain or branched chain of one to six carbon atoms, including but not limited to, methyl, ethyl, propyl, isopropyl, butyl, isobutyl, t-butyl, pentyl, and hexyl; methyl, ethyl, propyl and isopropyl are preferred groups.

Alkoxy is O-alkyl, wherein alkyl is as defined above.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Examples of pharmaceutically acceptable cationic salts of a chemical compound of the invention include, without limitation, the sodium, the potassium, the calcium, the magnesium, the zinc, the aluminium, the lithium, the choline, the lysinium, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the chemical compound of the invention include examples of suitable prodrugs of the substances according to the invention including compounds modified at one or more reactive or derivatizable groups of the parent compound. Of particular interest are compounds modified at a carboxyl group, a hydroxyl group, or an amino group. Examples of suitable derivatives are esters or amides.

The chemical compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Isomers

It will be appreciated by those skilled in the art that the compounds of the present invention may exist in different stereoisomeric forms—including enantiomers, diastereomers and cis-trans-isomers.

The invention includes all such isomers and any mixtures thereof including racemic mixtures.

Methods for the resolution of optical isomers, known to those skilled in the art may be used, and will be apparent to the average worker skilled in the art. Such methods include those discussed by J. Jaques, A. Collet, and S. Wilen in "Enantiomers, Racemates, and Resolutions", John Wiley and Sons, New York (1981).

Optical active compounds can also be prepared from optical active starting materials or intermediates.

Labelled Compounds

The compounds of the invention may be used in their labelled or unlabelled form. In the context of this invention the labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radio-nuclide as a label. Positron emitting radionuclides are all candidates for usage. In the context of this invention the radionuclide is preferably selected from $^2$H (deuterium), $^3$H (tritium), $^{13}$C, $^{14}$C, $^{131}$I, $^{125}$I, $^{123}$I, and $^{18}$F.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Methods of Preparation

The compounds of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The compounds of the present invention are useful as blockers of chloride channels or modulators of $BK_{Ca}$ channels.

Preferred compounds of the invention show a biological activity in the sub-micromolar and micromolar range, i.e. of from below 1 to about 100 µM.

Examples of types of chloride channels are Volume regulated anion channels (VRAC) or chloride channels of osteoclasts or erythrocytes. For measuring the activity of the compounds, various chloride channel blocking assays known in the art can be used.

Thus in a further aspect, the compounds of the invention are considered useful for the treatment, prevention or alleviation of a disease, disorder or condition responsive to the blockade of chloride channels.

In a special embodiment, the compounds of the invention are considered useful for the treatment, prevention or alleviation of:
  a bone metabolic disease, such as an osteoclast related bone disease, such as osteoporosis, postmenopausal osteoporosis, secondary osteoporosis, osteolytic breast cancer bone metastasis, osteolytic cancer invation, or Paget's disease of bone;
  diseases that are responsive to inhibition of angiogenesis, such as diseases that involve the proliferation of tumor cells, such as cancer, metastatic cancer, prostate cancer, lung cancer, breast cancer, bladder cancer, renal cancer, colon cancer, gastric cancer, pancreatic cancer, ovarian cancer, melanoma, hepatoma, sarcoma, lymphoma;
  ophthalmic angiogenesis related diseases, such as exudative macular degeneration, age-related macular degeneration (AMD), retinopathy, diabetic retinopathy, proliferative diabetic retinopathy, diabetic macular edema (DME), ischemic retinopathy (e.g. retinal vain or artery occlusion), retinopathy of prematurity, neovascular glaucoma, and corneal neovascularization; and
  disease, disorder or condition that is responsive to reduction of intraocular pressure, such as ocular hypertension, open-angle glaucoma, chronic open-angle glaucoma, angle-closure glaucoma and ciliary injection caused by angle-closure glaucoma,
  rheumatoid arthritis, psoriasis and
  sickle-cell anaemia.

In a further aspect, the compounds of the invention are considered useful for the treatment, prevention or alleviation of a disease, disorder or condition responsive to the modulation of $BK_{Ca}$ channels.

In a special embodiment, the compounds of the invention are considered useful for the treatment, prevention or alleviation of:
  a cardiovascular disease, such as atherosclerosis, ischemia, reperfusion injury, hypertension, restenosis, arterial inflammation, myocardial ischaemia or ischaemic heart disease;
  an obstructive or inflammatory airway disease, such as airway hyperreactivity, pneumoconiosis, aluminosis, anthracosis, asbestosis, chalicosis, ptilosis, siderosis, silicosis, tabacosis, byssinosis, sarcoidosis, berylliosis, pulmonary emphysema, acute respiratory distress syndrome (ARDS), acute lung injury (ALI), acute or chronic infectious pulmonary disease, chronic obstructive pulmonary disease (COPD), bronchitis, chronic bronchitis, wheezy bronchitis, excerbation of airways hyperreactivity or cystic fibrosis, or cough including chronic cough, excerbation of airways hyperreactivity, pulmonary fibrosis, pulmonary hypertension, inflammatory lung diseases, or acute or chronic respiratory infectious diseases,
  urinary incontinence, psychosis, epilepsy or pain.

Further, the compounds of the invention may also be well suited for facilitating the transport of therapeutic substances across the blood-brain barrier, and in particular for facilitating the transvascular delivery of chemotherapeutic agents and viral particles to tumour cells and other abnormal brain tissues.

Therefore, in another aspect, the invention relates to the use of a compound of the invention as a facilitating agent, useful for increasing the blood-brain barrier permeability, and thus capable of facilitating transport of a therapeutic substance across the blood-brain barrier, including the blood-tumour barrier found in brain tumours.

In one embodiment of this aspect the compound of the invention is used for facilitating agents to an abnormal brain region of brain tissue physiologically affected by injury, trauma, infection, stroke, or ischemia. This abnormal brain region is a region of benign or malignant tumor tissue or other neoplastic diseases or conditions. The malignant tumor may in particular be a glioma, glioblastoma, oligodendroglioma, astrocytoma, ependymoma, primitive neuroectodermal tumor, atypical meningioma, malignant meningioma, neuroblastoma, sarcoma, melanoma, lymphoma, or carcinoma.

When used as a facilitating agent, the compound of the invention may be co-administered with the therapeutic agent by any appropriate route, in any convenient way. Preferably, the facilitating agent is administered simultaneously (i.e. contemporaneously or concurrently), or substantially simultaneously (i.e. within about one hour, preferably within 30 minutes, even more preferred within 15 minutes) with the therapeutic agent.

The agents for use according to the invention, i.e. both the facilitating agent and the therapeutic agent, may be administered by any appropriate route, by which the agent is delivered to the blood stream. This is preferably done by intravenous, intramuscular or intra-arterial injection or infusion.

The therapeutic agent for use according to the invention may be any agent or drug. However, preferred therapeutic agents or drugs for use according to the invention are antineoplastic agents, chemotherapeutic agents, cytotoxic agents, DNA expression vectors, proteins, oligonucleotides, nucleotide analogs, antimicrobial agents, interferons, cytokines, cytokine agonists, cytokine antagonists, immunotoxins, immunosuppressants, boron compounds, monoclonal antibodies, adrenergic agents, anticonvulsants, ischemia-protective agents, anti-trauma agents, anticancer chemotherapeutic agents and diagnostic agents.

Preferred chemotherapeutic agents for use according to the invention include:

alkylating agents like the nitrogen mustards (e.g. mechlorethamine, cyclophosphamide, ifosamide, melphalan and chlorambucil), ethylenimines and methylmelamines (e.g. hexamethylmelamine and thiotepa), alkyl sulfonates (e.g. busulfan), nitrosoureas (e.g. carmustine (BCNU), lomustine (CCNU), semustine (methyl-CCNU) and streptozocin), triazenes (e.g. dacarbazine (DTIC));

antimetabolites like folic acid analogs (e.g. methotrexate), pyrimidine analogs (e.g. fluorouracil, floxuridine and cytarabine), purine analogs and related inhibitors (e.g. mercaptopurine, thioguanine and pentostatin); and natural antimitotic products like vinca alkaloids (e.g. vinblastine and vincristine), epipodophyllotoxins (e.g. etoposide and teniposide), antibiotics (e.g. dactinomycin, daunorubicin, doxorubicin, bleomycin, plicamycin and mitomycin), enzymes (e.g. L-asparaginase), a platinum coordination complex (e.g. cisplatin and carboplatin) and biological response modifiers like the interferons (e.g. interferon-α).

In another preferred embodiment the DNA expression vector is a viral vector, preferably an adenovirus-derived vector or herpes simplex virus-derived vector.

In yet another preferred embodiment the diagnostic agent for use according to the invention may in particular be an imaging or contrast agent, and it may in particular be a radioactively labelled substance, a gallium-labelled substance, or a contrast agent selected from the group consisting of ferrous magnetic, fluorescent, luminescent, and iodinated contrast agents.

When used as a facilitating agent, the compound of the invention may preferably be co-administered with the therapeutic agent for targeting regions of brain tissue physiologically directly affected by a physical or biochemical injury, for example Alzheimer's disease, Parkinson's disease, Parkinsonism, trauma, infection, stroke, brain ischemia, or regions of neoplastic growth within the brain, such as benign or malignant brain tumour tissues.

Methods of Therapy

In another aspect the invention provides a method for the treatment, prevention or alleviation of a disease or a disorder or a condition of a living animal body, including a human, which disease, disorder or condition is responsive to responsive to the blockade of chloride channels or modulation of $BK_{Ca}$ channels, and which method comprises administering to such a living animal body, including a human, in need thereof an effective amount of a chemical compound of the invention.

The preferred medical indications contemplated according to the invention are those stated above.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge. When administered in combination with compounds known in the art for treatment of the diseases, the dosis regimen may be reduced.

Combined Therapy

Use of the compounds of the invention may be combined with the use of other compounds useful for the treatment, prevention or alleviation of a disease, disorder or condition responsive to the blockade of chloride channels.

As an example, the compounds may be used in combination with one or more additional drugs useful for the treatment, prevention or alleviation of a disease responsive to inhibition of angiogenesis, such as compounds useful for anti-metastatic treatment. Such additional drugs include cytotoxic compounds, antimitotic compounds, and antimetabolites.

Examples of cytotoxic compounds (including cytotoxic alkylating agents) include carmustine (BCNU), fotemustin, temozolomide (temodal), ifosfamide, and cyclofosfamide.

Examples of antimitotic compounds include paclitaxel (taxol) and docetaxel.

An example of antimetabolites includes methotrexat.

Furthermore, the pharmaceutical composition for use according to the invention may be used or administered in combination with other treatments or therapies. Examples of other treatments or therapies include radiotherapy and surgery.

Also, use of the compounds of the invention may be combined with the use of other bone metabolism controlling compounds for the treatment of bone metabolic disease. Such known bone metabolism controlling compounds include bisphophonates such as etidronate, pamidronate, or clodronate optionally combined with calcium; oestrogen-receptor active compounds such as oestrogen i.e. oestradiol and ethyloestradiol, calcitonin, 1,25-dihydroxyvitamine D and metabolites thereof, fluoride, growth hormone, parathyroid hormone, triiodo-thyrosine, collagen degrading enzymes such as protease inhibitors, or cancer therapeutic agents.

Also, use of the compounds of the invention may be combined with the use of one or more additional drugs useful for the treatment, prevention or alleviation of a disease, disorder or condition is responsive to reduction of intraocular pressure. Such additional drugs include beta-blockers, parasympathomimetic miotics, sympathomimetics, and carbonic anhydrase inhibitors.

Furthermore, use of the compounds of the invention may be combined with other treatments or therapies.

The treatment of the diseases and disorder can be in chronical or a long term treatment as well as a treatment of sudden crisis in the disease and disorder.

Pharmaceutical Compositions

In another aspect the invention provides novel pharmaceutical compositions comprising a therapeutically effective amount of the chemical compound of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention, or a pharmaceutically acceptable salt or derivative thereof, together with one or more pharmaceutically acceptable carriers, and, optionally, other therapeutic and/or prophylactic ingredients, known and used in the art. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient, which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions exhibiting large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

EXAMPLES

The invention is further illustrated with reference to the following examples, which are not intended to be in any way limiting to the scope of the invention as claimed.

Example 1

4-Amino-4'-trifluoromethyl-biphenyl-3-carbonitrile

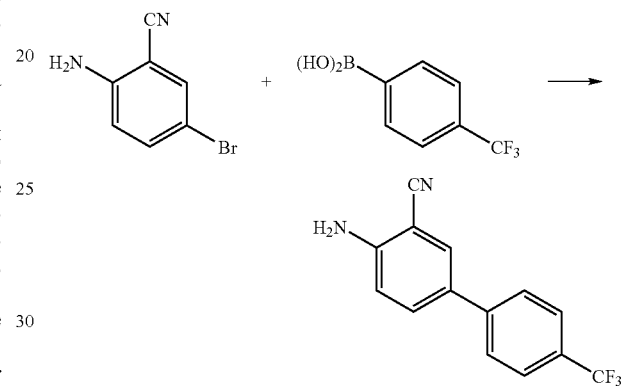

In 250 ml of water and 500 ml of 1,2-dimethoxyethane, was mixed 26.5 g of 4-(trifluoromethyl)benzeneboronic acid, 25 g of 2-amino-5-bromo-benzonitrile and 57.9 g of potassium carbonate. The mixture was bobbled through with nitrogen for 10 minutes, then 1 g of bis(triphenylphosphine)palladium(II) choride was added and the reaction mixture was heated at reflux overnight. The reaction mixture was cooled to room temperature, added 700 ml of water and extracted with 800 ml of ethyl acetate. The organic phase was washed first with 300 ml of saturated sodium chloride, then 300 ml of 2 M calcium chloride and at last with 300 ml of water. The organic phase was dried with magnesium sulfate, evaporated to an oil and trituated with ether. Yield 30.5 g (92%).

Example 2

4-Amino-N-hydroxy-4'-trifluoromethyl-biphenyl-3-carboxamide

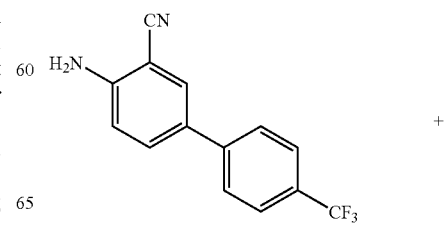

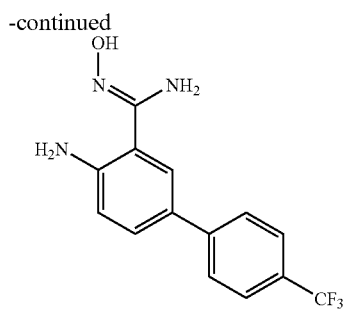

4-Amino-4'-trifluoromethyl-biphenyl-3-carbonitrile (10 g) was dissolved in 250 ml of methanol and added 5.6 g of hydroxylamine hydrochloride and 8.1 g of triethylamine. The reaction mixture was stirred at 50° C. overnight, added 100 ml of water and 100 ml of ethyl acetate. The water phase was extracted with 100 ml of ethyl acetate. The organic phases was washed with 100 ml water and after that with 100 ml saturated sodium chloride. The organic phase was dried with magnesium sulfate and evaporated to an oil. Yield 10.8 g (96%).

Example 3

3-(4-Amino-4'-trifluoromethyl-biphenyl-3-yl)-4H-[1,2,4]-oxadiazol-5-one

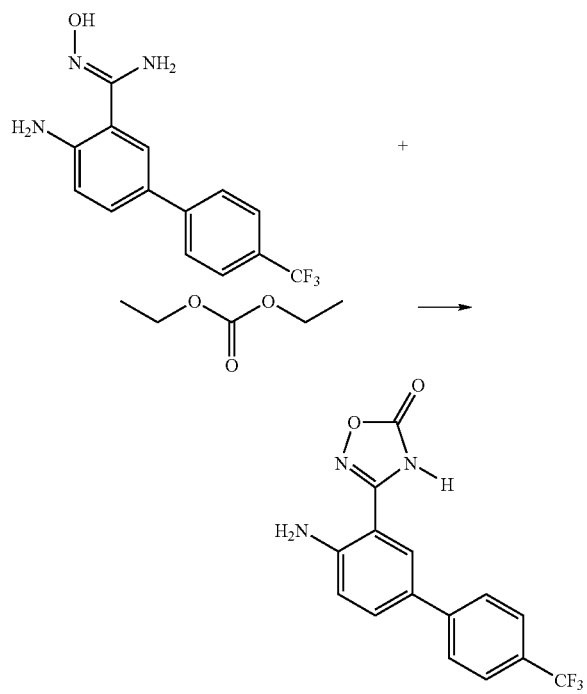

Sodium (1.6 g) was stirred in 200 ml dry ethanol until it was dissolved, to the solution was added 10.8 g of 4-amino-N-hydroxy-4'-trifluoromethyl-biphenyl-3-carboxamide and 16 g of diethyl carbonate, the reaction mixture was stirred overnight at 85° C., evaporated to an oil, the residue was dissolved in ethyl acetate, the organic phase was extracted with 4 N aqueous NaOH. The aqueous phase was made acidic with conc. hydrochloric acid and extracted with ethyl acetate. The organic phase was washed with saturated aqueous sodium chloride, dried with magnesium sulfate and evaporated to an oil. The residue was dissolved in 150 ml of boiling ethanol. The solution was cooled to room temperature the product crystallized, was isolated by filtration and dried. Yield 5.1 g (45%).

Example 4

N-(3,5-Difluoro-phenyl)-N'-[3-(5-oxo-4,5-dihydro-[1,2,4]oxadiazol-3-yl)-4'-trifluoromethyl-biphenyl-4-yl]urea

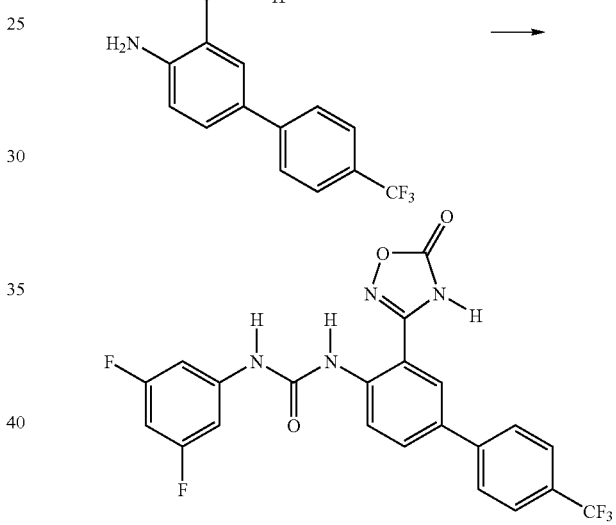

In 100 ml of dry toluene was 5 g of 3-(4-amino-4'-trifluoromethyl-biphenyl-3-yl)-4H-[1,2,4]oxadiazol-5-one suspended and 2.5 g of 3,5-difluorophenyl isocyanate was added, the reaction mixture was stirred at room temperature overnight, 1.3 g of 3,5-difluorophenyl isocyanate was added and stirring was continued overnight. 3,5-Difluorophenyl isocyanate (1.3 g) and 100 ml of acetonitrile was added, the reaction mixture was stirred at room temperature for 90 min. and evaporated to dryness. The residue was dissolved in 100 ml of boiling acetone, then cooled to 0° C. and filtrated. The precipitate was recrystallized from 200 ml of ethanol, after filtration while hot, the solution was added 400 ml of water. The product was isolated by filtration. Yield 4 g (54%) mp.>150° C. decomp.

Analogously was made:

N-(4-Chloro-3-trifluoromethyl-phenyl)-N'-{3-(5-oxo-4,5-dihydro-[1 ,2,4]-oxadiazol-3-yl)-4'-trifluoromethyl-biphenyl-4-yl}urea: Mp>139° C. decomp.

N-(3-Bromo-phenyl)-N'-{3-(5-oxo-4,5-dihydro-[1,2,4]-oxadiazol-3-yl)-4-trifluoromethyl-biphen-4-yl}urea. Mp>200° C. decomp.

N-(2-Chloro-phenyl)-N'-{3-(5-oxo-4,5-dihydro-[1,2,4]-oxadiazol-3-yl)-4-trifluoromethyl-biphenyl-4-yl]urea. Mp 220-222° C.

Example 5

In Vitro Human Erythrocyte Chloride Conductance

The chloride conductance was measured according to the proceeding as described in the "Biology" paragraph of the specification of WO 00/24707. The parameter calculated from these studies is the $IC_{50}$ value—the concentration at which 50% of the chloride channels are blocked.

The first compound of Example 4, N-(3,5-Difluoro-phenyl)-N'-[3-(5-oxo-4,5-dihydro-[1,2,4]oxadiazol-3-yl)-4'-trifluoromethyl-biphenyl-4-yl]urea, shows an $IC_{50}$ value of 0.28 μM.

Example 6

Volume Regulated Anion Channel (VRAC) Effect

The activity on the Volume Regulated Anion Channel (VRAC) was tested by the whole cell patch clamp technique using Human Embryonic Kidney cells (HEK293) as described in Helix et al, J Membr Biol. 2003 196(2):83-94, In short, VRAC was activated by swelling of the cell in hypotonic (75% tonicity) extracellular salt solution and the anion current elicited by voltage ramps was measured vs. time. After stabilization of the current the compound to be tested was added to the extracellular solution and the time dependent block was followed for calculation of the $K_D$ value. The first compound of Example 4, N-(3,5-Difluoro-phenyl)-N'-[3-(5-oxo-4,5-dihydro-[1,2,4]oxadiazol-3-yl)-4'-trifluoromethyl-biphenyl-4-yl]urea, shows a $K_D$ value of 0.23 μM

Example 7

Human BK Channel Screening

The influence of a compound on the membrane currents was determined electrophysiologically on *Xenopus Oocytes* capable of expressing human BK channels, and the current through the channels was recorded using the classical two-electrode voltage clamp technique.

The first compound of Example 4, N-(3,5-Difluoro-phenyl)-N'-[3-(5-oxo-4,5-dihydro-[1,2,4]oxadiazol-3-yl)-4'-trifluoromethyl-biphenyl-4-yl]urea, was subjected to this determination at a concentrations of 0.3 μM of test compound, and it caused an increase of BK current relative to the basal current of more than 200%.

The invention claimed is:

1. A chemical compound of Formula (I)

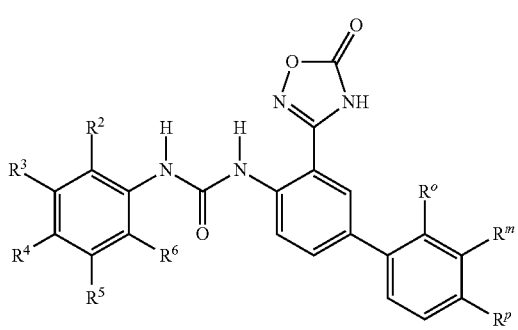

(I)

any of its stereoisomers or any mixture of its stereoisomers, or a pharmaceutically acceptable salt thereof; wherein $R^o$, $R^m$, $R^p$, $R^2$, $R^3$, $R^4$, $R^5$ and $R^6$ independently of each other represent hydrogen, halo, trifluoromethyl, trifluoromethoxy, alkyl or alkoxy.

2. The compound of claim 1, or a pharmaceutically acceptable salt thereof, wherein
   $R^o$ represents hydrogen;
   $R^m$ represents hydrogen; and
   $R^p$ represents halo, trifluoromethyl, trifluoromethoxy, alkyl or alkoxy.

3. The compound of claim 1, or a pharmaceutically acceptable salt thereof, wherein
   $R^o$ represents hydrogen;
   $R^m$ represents hydrogen; and
   $R^p$ represents halo or trifluoromethyl.

4. The compound of claim 1, or a pharmaceutically acceptable salt thereof, wherein
   $R^3$, $R^4$, $R^5$ and $R^6$ represent hydrogen; and
   $R^2$ represents halo, trifluoromethyl, trifluoromethoxy, alkyl or alkoxy.

5. The compound of claim 1, or a pharmaceutically acceptable salt thereof, wherein
   $R^2$, $R^4$, $R^5$ and $R^6$ represent hydrogen; and
   $R^3$ represents halo, trifluoromethyl, trifluoromethoxy, alkyl or alkoxy.

6. The compound of claim 1, or a pharmaceutically acceptable salt thereof, wherein
   $R^2$, $R^5$ and $R^6$ represent hydrogen; and
   $R^3$ and $R^4$ independently of each other represent halo, trifluoromethyl, trifluoromethoxy, alkyl or alkoxy.

7. The compound of claim 1, or a pharmaceutically acceptable salt thereof, wherein
   $R^2$, $R^4$ and $R^6$ represent hydrogen; and
   $R^3$ and $R^5$ independently of each other represent halo, trifluoromethyl, trifluoromethoxy, alkyl or alkoxy.

8. The compound of claim 1, which is
   N-(3,5-Difluoro-phenyl)-N'-[3-(5-oxo-4,5-dihydro-[1,2,4]oxadiazol-3-yl)-4'-trifluoromethyl-biphenyl-4-yl] urea;
   N-(4-Chloro-3-trifluoromethyl-phenyl)-N'-{3-(5-oxo-4,5-dihydro-[1,2,4]-oxadiazol-3-yl)-4'-trifluoromethyl-biphenyl-4-yl} urea;
   N-(3-Bromo-phenyl)-N'-{3-(5-oxo-4,5-dihydro-[1,2,4]-oxadiazol-3-yl)-4'-trifluoromethyl-biphen-4-yl} urea;
   N-(2-Chloro-phenyl)-N'-{3-(5-oxo-4,5-dihydro-[1,2,4]-oxadiazol-3-yl)-4'-trifluoromethyl-biphenyl-4-yl] urea;
   or a pharmaceutically acceptable salt thereof.

9. A pharmaceutical composition comprising a therapeutically effective amount of a compound according to claim 1, any of its stereoisomers or any mixture of its stereoisomers, or a pharmaceutically acceptable salt thereof, together with at least one pharmaceutically acceptable carrier, excipient or diluent.

10. A method for increasing the blood-brain barrier permeability of a living animal body, including a human, which method comprises the step of administering to such a living animal body in need thereof a therapeutically effect amount of a compound according to claim 1, any of its stereoisomers, or any mixture of its stereoisomers, or a pharmaceutically acceptable salt thereof.

* * * * *